(12) United States Patent
Evans et al.

(10) Patent No.: US 11,931,011 B1
(45) Date of Patent: Mar. 19, 2024

(54) TELESCOPE MAINTENANCE DEVICES AND ASSEMBLIES

(71) Applicants: Robert Michael Evans, Santa Fe, NM (US); George Crawford, Anniston, AL (US)

(72) Inventors: Robert Michael Evans, Santa Fe, NM (US); George Crawford, Anniston, AL (US)

( * ) Notice: Subject to any disclaimer, the term of this patent is extended or adjusted under 35 U.S.C. 154(b) by 38 days.

(21) Appl. No.: 17/952,276

(22) Filed: Sep. 25, 2022

(51) Int. Cl.
*A61B 1/12* (2006.01)
*A61B 1/00* (2006.01)
*A61B 1/313* (2006.01)

(52) U.S. Cl.
CPC .......... *A61B 1/126* (2013.01); *A61B 1/00154* (2013.01); *A61B 1/127* (2013.01); *A61B 1/3132* (2013.01)

(58) Field of Classification Search
CPC ..... A61B 1/126; A61B 1/00154; A61B 1/127; A61B 1/3132; A61B 18/1487; A61B 2017/349; A61B 2017/348; A61B 2017/047; A61B 2017/00637; A61M 2039/0626; A61M 5/00; A61J 1/2096; A61J 1/20
See application file for complete search history.

(56) References Cited

U.S. PATENT DOCUMENTS

| | | | |
|---|---|---|---|
| 9,033,929 B2 * | 5/2015 | Moreno | A61B 17/3462 604/167.03 |
| 9,050,037 B2 | 6/2015 | Poll et al. | |
| 9,078,694 B2 | 7/2015 | Hartoumbekis et al. | |
| 10,751,085 B2 | 8/2020 | Rosenbaum et al. | |
| 11,076,848 B2 * | 8/2021 | Malkowski | A61M 5/329 |
| 11,202,559 B2 | 12/2021 | Mulcahey et al. | |
| 2015/0374915 A1 * | 12/2015 | Hyde | A61M 5/142 604/152 |
| 2018/0214016 A1 | 8/2018 | Thommen et al. | |
| 2019/0110674 A1 | 4/2019 | Allen et al. | |

FOREIGN PATENT DOCUMENTS

WO    1996014013 A1    5/1996

* cited by examiner

*Primary Examiner* — Michael J Carey
*Assistant Examiner* — Megan Elizabeth Monahan
(74) *Attorney, Agent, or Firm* — Andrea Hence Evans; The Law Firm of Andrea Hence Evans, LLC

(57) ABSTRACT

Devices for maintaining a telescope during a minimally invasive surgery (MIS) technique such as laparoscopy or thoracoscopy. A telescope maintenance assembly is comprised of a disc and a dome. The disc is absorbent and includes a central aperture. The dome is hollow and includes an inlet port, a lower protrusion, and outlet ports which abut against the disc when attached thereto. To prepare the assembly for use, the disc is secured about a proximal port of a trocar and the lower protrusion is inserted through the central aperture, and an anti-fog solution is transmitted into and through the dome to wet the disc. After the disc is wetted, the wetted disc can be used by a surgeon or assistant to wipe debris from a lens or other optical component of the telescope without needing to remove the telescope from the trocar.

7 Claims, 10 Drawing Sheets

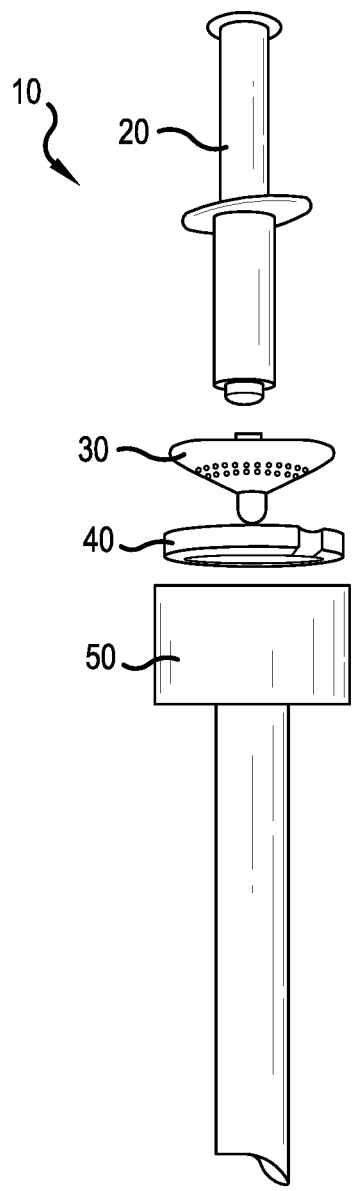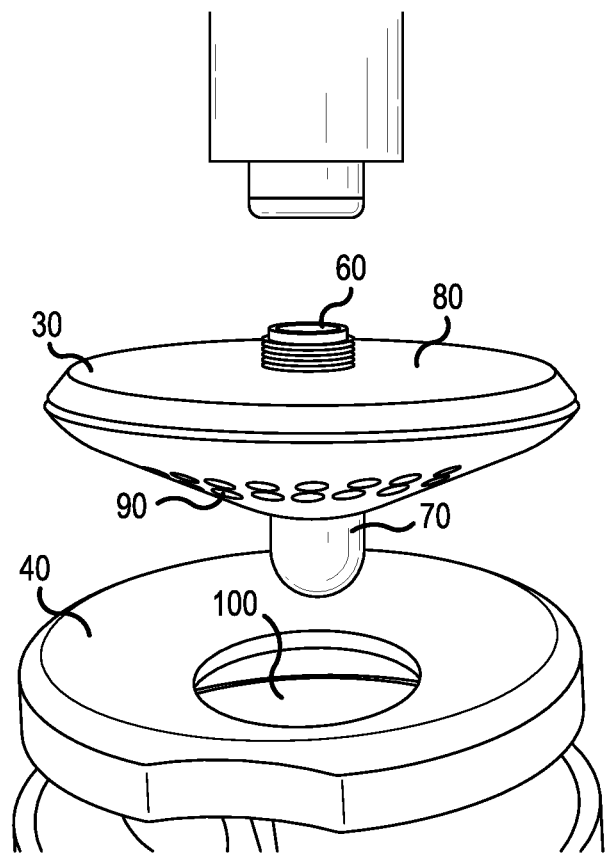
FIG.1A
FIG.1B

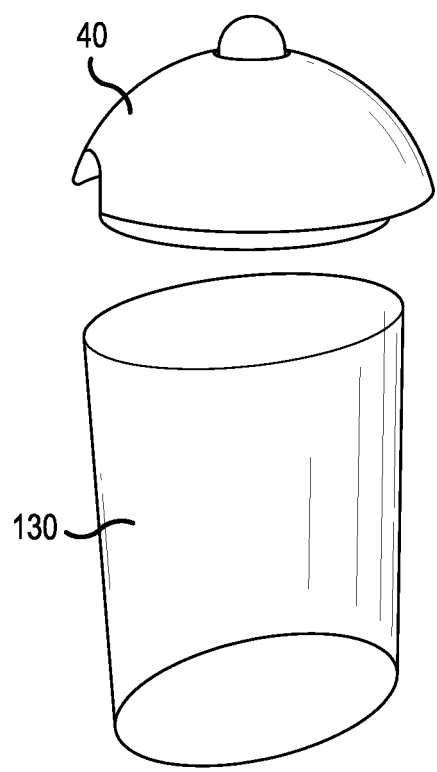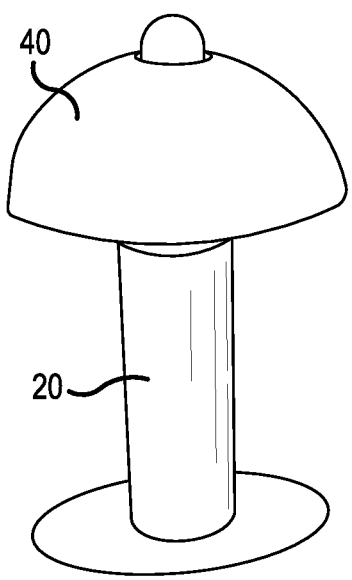
FIG.2E
FIG.2F

TELESCOPE MAINTENANCE DEVICES AND ASSEMBLIES

FIELD

The disclosure relates to devices and assemblies for maintaining a telescope during a minimally invasive surgery (MIS) technique such as laparoscopy or thoracoscopy. A telescope maintenance assembly includes a disc and a dome. The disc can be secured about a proximal trocar port and wetted with an anti-fog solution using the dome. The secured and wetted disc can be used by a surgeon or assistant to wipe debris from a lens or other optical component of the telescope without needing to remove the telescope from the trocar.

BACKGROUND

Many minimally invasive surgery (MIS) procedures utilize a scoping procedure, such as laparoscopy or thoracoscopy, so that medical personnel can view the interior of the body and coordinate the procedure visually. Maintaining visibility of interior body structures is critical for reducing risk of injury to the patient due to misplaced surgical tools, which can easily puncture soft tissue and complicate the procedure or endanger the patient. However, frequently, optical elements of a telescope used in such techniques are colder than the interior of the body and accumulate fog or other debris, which interferes with light capture and obstructs the view of the operator and medical personnel. This can lead to a greater risk of misplacement of surgical tools and injury to the patient.

In response to the obstructed view, personnel must clear away the fog or debris to optimal visualization provided by the telescope. Existing methods for clearing away the lens or other optical element include the use of battery-powered cleaning devices, special sheaths, and in the case of fog, a warming thermos to bring the lens or optical element up to a higher temperature such that fog or condensation does not accumulate thereon when inserted into the humid environment of the interior of the patient. Other approaches include the use of sponges and anti-fog solutions. While these approaches may be effective at cleaning the telescope in some circumstances, they are not convenient and generally require the surgeon or telescope operator to remove the telescope from the trocar, perform the cleaning, and return the telescope to the trocar. This process is time-consuming and labor-intensive, and in some instances, results in a renewed accumulation of fog and debris to the distal end of the telescope lens due to the telescope and optical elements returning to a lower temperature while being cleaned outside of the body. As a result of all this back and forth, the time of the surgery is extended, the patient is exposed to anesthetic for greater periods of time, and the risk of the surgeon losing their orientation or vision of the procedure increases, which can prolong and further complicate the procedure.

Accordingly, there is a need for an approach for quickly and effectively cleaning lenses and optical elements of telescopes that does not require the surgeon or telescope operator to remove the telescope entirely from the trocar. The present invention addresses this unmet need.

SUMMARY

In one aspect, the disclosure provides an assembly for maintaining and visualization of a telescope for a minimally invasive surgery (MIS) technique, the assembly comprising an absorbent disc with a central aperture and a hollow dome having an inlet port, a lower protrusion, and a plurality of outlet ports. The absorbent disc is configured to be secured about a proximal port of a trocar by insertion of the lower protrusion through the central aperture and application of an attachment force thereto and the absorbent disc is configured to be wetted by delivery of a solution through the inlet port to an interior of the hollow dome and out of the plurality of outlet ports to contact and wet the absorbent disc. Once it is wetted, the absorbent disc can be used to clean the telescope quickly and easily during the MIS technique without needing to remove the telescope from the trocar.

In another aspect, the disclosure provides a hollow dome for an assembly for maintaining a telescope for a minimally invasive surgery (MIS) technique, the hollow dome comprising an inlet port, a lower protrusion, and a plurality of outlet ports. The inlet port is configured to receive a solution therethrough to contact an interior of the hollow dome and flow out of the plurality of outlet ports. Since the hollow dome is configured to snugly abut against the absorbent disc along the outlet ports, it can be used to wet the absorbent disc quickly and easily during the MIS technique using a syringe, a bottle, or another source of a suitable liquid or solution such as anti-fog solution.

In yet another aspect, the disclosure provides a method for maintaining a telescope for a minimally invasive surgery (MIS) technique, the method comprising securing an absorbent disc about a proximal port of a trocar, wetting the absorbent disc with a solution, and contacting the telescope to the absorbent disc to remove fog, condensation, or debris from the telescope for continued use of the telescope in the MIS technique. The absorbent disc includes a central aperture configured to receive the telescope therethrough, and the contacting the telescope to the absorbent disc may involve slidingly moving the telescope through the central aperture of the wetted disc to contact the telescope, e.g., an optical element of the telescope such as a lens or transparent casing, against the wetted disc to clean the telescope for immediate continued use during the MIS technique.

The invention generally relates to telescope maintenance or cleaning assemblies, devices, and components which may be manufactured with appropriate materials and processes and which may be scaled as needed.

Other objects, features, and advantages of the invention will become apparent from the following detailed description taken in conjunction with the accompanying drawings.

BRIEF DESCRIPTION OF THE DRAWINGS

Although the characteristic features of the invention will be particularly pointed out in the claims, the invention itself and manners in which it may be made and used may be better understood after a review of the following description, taken in connection with the accompanying drawings, wherein like numeral annotations are provided throughout.

FIG. 1A shows a perspective view of an exemplary assembly for maintaining a telescope for a minimally invasive surgery (MIS) technique, positioned near a trocar and a syringe.

FIG. 1B shows a close-up perspective view of the exemplary assembly.

FIG. 2E shows a perspective view of the assembly in an upside-down orientation with an absorbent disc attached to the dome of the assembly with the bottle solution dispenser thereon.

FIG. 2F shows a perspective view of the assembly in an upside-down orientation with the absorbent disc attached to the dome of the assembly with the syringe solution dispenser thereon.

DETAILED DESCRIPTION OF THE INVENTION

Figure 1C:
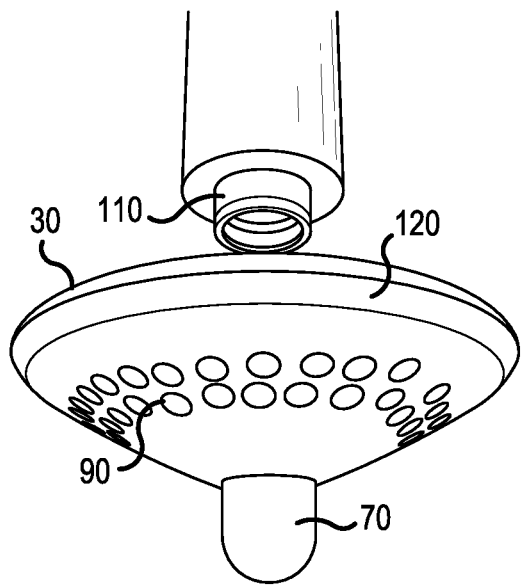
FIG. 1C shows a lower close-up perspective view of the exemplary assembly, with an emphasis on a plurality of outlet ports of a hollow dome of the assembly.

Reference is made herein to the attached drawings. Like reference numerals may be used in the drawings to indicate like or similar elements of the description. The figures are intended for representative purposes and should not be considered limiting.

The present disclosure can be understood more readily by reference to the following detailed description of the present disclosure and the examples included therein.

Before the present articles, systems, devices, and/or methods are disclosed and described, it is to be understood that they are not limited to specific implementations unless otherwise specified, or to particular approaches unless otherwise specified, as such can, of course, vary. It is also to be understood that the terminology used herein is for the purpose of describing aspects only and is not intended to be limiting. Although any methods and materials similar or equivalent to those described herein can be used in the practice or testing of the present disclosure, example methods and materials are now described.

All publications mentioned herein are incorporated herein by reference to disclose and describe the methods and/or materials in connection with which the publications are cited.

Definitions

It is to be understood that the terminology used herein is for the purpose of describing particular aspects only and is not intended to be limiting. As used in the specification and in the claims, the term "comprising" can include the aspects "consisting of" and "consisting essentially of" Unless defined otherwise, all technical and scientific terms used herein have the same meaning as commonly understood by one of ordinary skill in the art to which this present disclosure belongs. In this specification and in the claims which follow, reference will be made to a number of terms which shall be defined herein.

As used in the specification and the appended claims, the singular forms "a," "an," and "the" include plural referents unless the context clearly dictates otherwise. Thus, for example, reference to "an opening" can include two or more openings.

Ranges can be expressed herein as from one particular value, and/or to another particular value. When such a range is expressed, another aspect includes from the one particular value and/or to the other particular value. Similarly, when values are expressed as approximations, by use of the antecedent 'about,' it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

The terms "first," "second," "first part," "second part," and the like, where used herein, do not denote any order, quantity, or importance, and are used to distinguish one element from another, unless specifically stated otherwise.

As used herein, the terms "optional" or "optionally" means that the subsequently described event or circumstance can or cannot occur, and that the description includes instances where said event or circumstance occurs and instances where it does not. For example, the phrase "optionally affixed to the surface" means that it can or cannot be fixed to a surface.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including matters of logic with respect to arrangement of steps or operational flow; plain meaning derived from grammatical organization or punctuation; and the number or type of aspects described in the specification.

Disclosed are the components to be used to manufacture the disclosed devices, systems, and articles of the present disclosure as well as the devices themselves to be used within the methods disclosed herein. These and other materials are disclosed herein, and it is understood that when combinations, subsets, interactions, groups, etc. of these materials are disclosed that while specific reference of each various individual and collective combinations and permutation of these materials cannot be explicitly disclosed, each is specifically contemplated and described herein. For example, if a particular material is disclosed and discussed and a number of modifications that can be made to the materials are discussed, specifically contemplated is each and every combination and permutation of the material and the modifications that are possible unless specifically indicated to the contrary. Thus, if a class of materials A, B, and C are disclosed as well as a class of materials D, E, and F and an example of a combination material, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the articles and devices of the present disclosure. Thus, if there are a variety of additional steps that can be performed it is understood that each of these additional steps can be performed with any specific aspect or combination of aspects of the methods of the present disclosure.

It is understood that the devices and systems disclosed herein have certain functions. Disclosed herein are certain structural requirements for performing the disclosed functions, and it is understood that there are a variety of structures that can perform the same function that are related to the disclosed structures, and that these structures will typically achieve the same result.

Figure 1D:
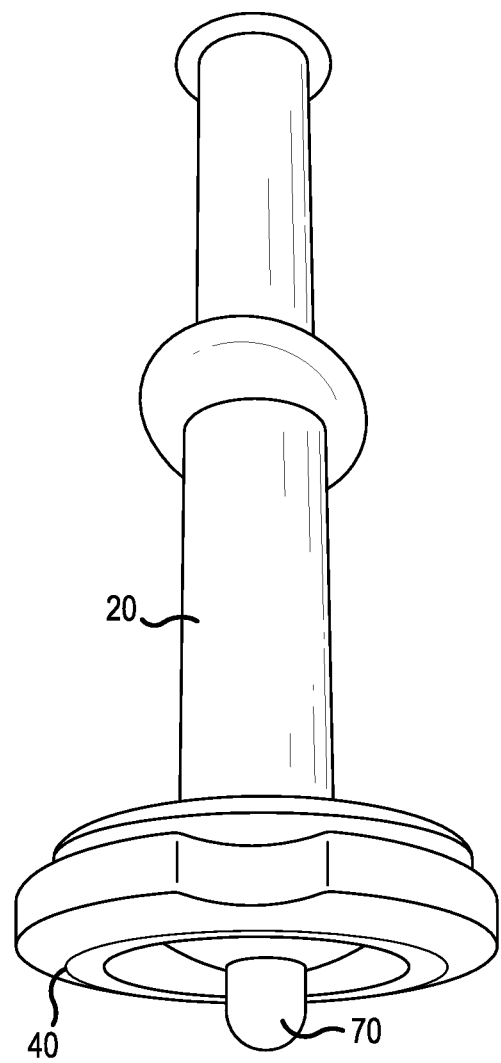
FIG. 1D shows a lower perspective view of the exemplary assembly, with the syringe attached to the hollow dome and an absorbent disc secured to the hollow dome in preparation for securement of the absorbent disc to the trocar and/or wetting of the absorbent disc.

Referring now to FIGS. 1A, 1B, 1C, and 1D, there are shown a perspective view of an exemplary assembly for maintaining a telescope for a minimally invasive surgery (MIS) technique, positioned near a trocar and a syringe (FIG. 1A), a close-up perspective view of the exemplary assembly (FIG. 1B), a lower close-up perspective view of the exemplary assembly, with an emphasis on a plurality of outlet ports of a hollow dome of the assembly (FIG. 1C), and a lower perspective view of the exemplary assembly, with the syringe attached to the hollow dome and an absorbent disc secured to the hollow dome in preparation for securement of the absorbent disc to the trocar and/or wetting of the absorbent disc (FIG. 1D).

In general, the present disclosure provides an assembly 10 for maintaining a telescope for a minimally invasive surgery (MIS) technique. The assembly 10 comprises an absorbent disc 40 with a central aperture 100 and a hollow dome 30 having an inlet port 60, a lower protrusion 70, and a plurality of outlet ports 90. The absorbent disc 40 is configured to be secured about a proximal port of a trocar 50 by insertion of the lower protrusion 70 through the central aperture 100 and application of an attachment force thereto. The absorbent disc 40 is configured to be wetted by delivery of a solution through the inlet port 60 to an interior of the hollow dome 30 and out of the plurality of outlet ports 90 to contact and wet the absorbent disc 40. The assembly 10 includes a variety of features that greatly facilitate its use for the maintenance of a telescope for a MIS technique, such as laparoscopy or thoracoscopy.

While the wetted disc 40 may be wetted directly without use of the hollow dome 30, the hollow dome 30 provides several advantages with its use. Because the hollow dome 30 is shaped to snugly fit against the absorbent disc 40, it can be used to wet the disc 40 and also apply the disc 40 to the proximal part of the trocar 50 as part of a single movement or operation. In addition, because the solution dispenser (whether it be a bottle, a syringe 20, or another solution dispenser) may be configured to deliver a volume of solution to the hollow dome 30, the outlet ports 90 of the hollow dome 30 ensure reliable and even wetting of the absorbent disc 40 with the volume of solution and reduce the risk of excess solution falling through the trocar 50 which may end up inside the body of the patient. In this manner the absorbent disc 40 is easily and reproducibly prepared for use during surgery and the surgeon or other personnel experience greater ease of use and consistency with preparing for the MIS technique and maintaining the telescope during the procedure.

In embodiments, the inlet port 60 is configured to connect with a slip tip connector (e.g., a Luer lock connector or other leak-free connector) of a syringe 20 or a bottle for leak-free delivery of the solution through the inlet port 60. Because the trocar 50 may be inserted into a body cavity of a patient, it is important that application of anti-fog solution to the absorbent disc 40 does not risk introduction of the solution into the body cavity of the patient or spill on the operating table or other sensitive space. In this manner, the surgical site is maintained according to the requisite degree of cleanliness and sanitation.

In embodiments, the hollow dome 30 is at least approximately cone-shaped, the inlet port 60 is positioned centrally at an upper portion 80 thereof, and the lower protrusion 70 is positioned centrally at a lower potion 120 thereof. The cone shape of the hollow dome 30 enables slants of the hollow dome 30 to snugly abut against portions of the absorbent disc 40 to facilitate securement of the absorbent disc 40 to the proximal port of the trocar 50. In various implementations the assembly 10 may be sized, shaped, and configured to be compatible with any trocar 50 from any manufacturer (i.e., a universal fit), but in other implementations, may be specifically sized, shaped, and configured to be compatible with a particular trocar design or a trocar 50 from a particular manufacturer. The considerations impacting selection of a particular form factor for the hollow dome 30 include shape of the trocar 50 or trocars 50 as well as parameters needed for reliable operation of the hollow dome 30 to wet the disc 40 during use.

In embodiments, the hollow dome 30 fits snugly with the absorbent disc 40 such that the plurality of outlet ports 90 directly contacts portions of the absorbent disc 40 when applied thereto. Because the anti-fog solution passes through the hollow dome 30 and out of the outlet ports 90, a close contact between the outlet ports 90 and the absorbent disc 40 may be beneficial to ensure that the solution does not spill out from the assembly 10 during use.

In embodiments, outlet ports 90 are positioned on a slant of the hollow dome 30. By positioning the outlet ports along the slant, the same surface that snugly contacts the absorbent disc 40 also introduces the solution to the absorbent disc 40 via the outlet ports 90. In this manner, the assembly 10 is easily assembled and effectively used.

In embodiments, outlet ports 90 are regularly spaced along a circumference of the slant of the hollow dome 30. While any particular spacing may be effective due to dispersion of the solution within the absorbent disc 40 after wetting, it may be beneficial to have the outlet ports 90 be regularly spaced to ensure even wetting of the disc 40. Some absorbent discs 40 may facilitate wicking of the solution from the point of contact at the outlet port 90 to adjacent portions of the disc 40 not directly contacted by the outlet port 90. Since wicking properties of the disc 40 may vary, the size and spacing of the outlet ports 90 may also vary. A greater number of smaller outlet ports 90, more closely spaced to one another, may help ensure even wetting across the surface of the absorbent disc 40, however, a smaller number of larger outlet ports 90, more distally spaced to one another, may help ensure deeper wetting through the depth of the absorbent disc 40. In this manner, the size, shape, spacing, number, and placement of the outlet ports 90 may be varied or optimized for use with particular materials or matrices used for the absorbent disc 40.

In embodiments, the plurality of outlet ports 90 includes an inner ring of outlet ports 90 and an outer ring of outlet ports 90, wherein a distance from the inner ring to the lower protrusion 70 is less than a distance from the outer ring to the lower protrusion 70. Having multiple rings of outlet ports 90 on the hollow dome 30 may help ensure even coverage of the disc 40 with anti-fog solution at various radial distances from the central aperture 100. Since dispersal of the solution within the disc 40 may be impacted by gravity such that the solution is inclined to flow downward toward the central aperture 100, this also helps ensure outer regions of the disc 40 are effectively wetted. In this manner, the surgeon or other personnel can easily wipe the telescope on any portion of the wetted disc 40 to clean the telescope for continued use.

In embodiments, the central aperture 100 is configured to slidingly accept the telescope therethrough. The central aperture 100 may be sized to snugly accept the telescope therethrough, or alternatively, may not substantially contact the telescope when the telescope is inserted therethrough. However, regardless of whether the wetted disc 40 snugly contacts the telescope at all times, the wetted disc 40 is positioned at the proximal port of the trocar 50 for convenient access and use by medical personnel to clean the telescope.

In embodiments, a sliding movement of the telescope through the central aperture 100 contacts the absorbent disc 40 against the telescope and clears fog or debris from the telescope for continued use of the telescope in the MIS technique. The design of the disc 40 to circumscribe the telescope helps ensure that medical personnel are able to easily wipe the telescope on the wetted disc 40 for cleaning, and in instances where there is fog, condensation, or debris along many different portions of the telescope, can help facilitate removal of those materials with limited movement of the telescope. In this manner, the surgeon or assistant is better able to maintain the positioning of the trocar 50 within the cavity of the body of the patient as well as the positioning of the telescope within the trocar 50, and the cleaning movement—which may involve a simple sliding removal of the telescope from a portion of the trocar 50 and re-insertion of the telescope into the portion of the trocar 50—is streamlined.

Figure 2A:
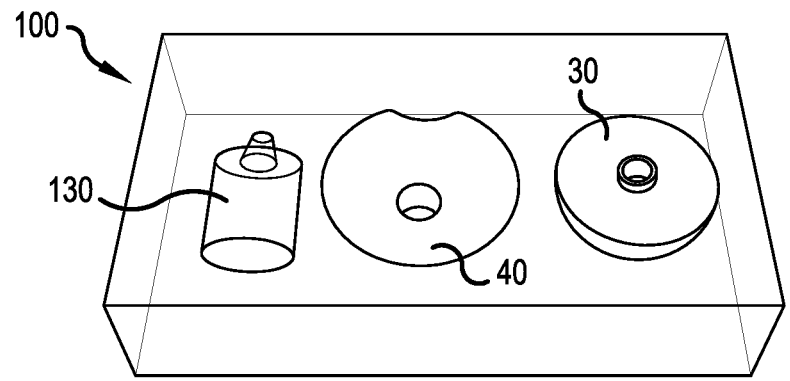
FIG. 2A shows a perspective view of components of an exemplary assembly with a bottle solution dispenser.
Figure 2B:
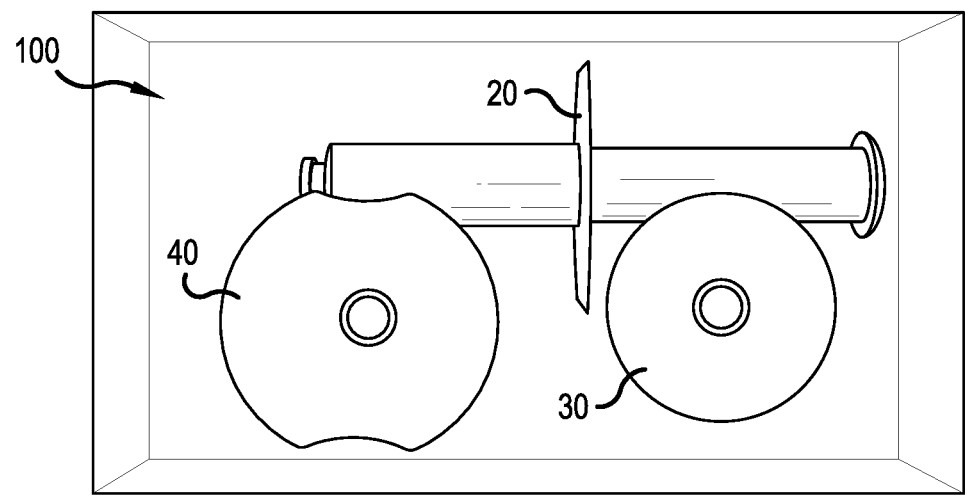
FIG. 2B shows a perspective view of components of an exemplary assembly with a syringe solution dispenser.

Referring now to FIGS. 2A and 2B, there are shown a perspective view of components of an exemplary assembly 10 with a bottle solution dispenser 130 (FIG. 2A) and a perspective view of components of an exemplary assembly with a syringe solution dispenser 20 (FIG. 2B). The assembly 10 may be configured for use with any suitable source of liquid or solution, such as cleaning solution or anti-fog solution, as may be stored in and delivered from a bottle 130 or a syringe 20, among other forms.

Figure 2C:
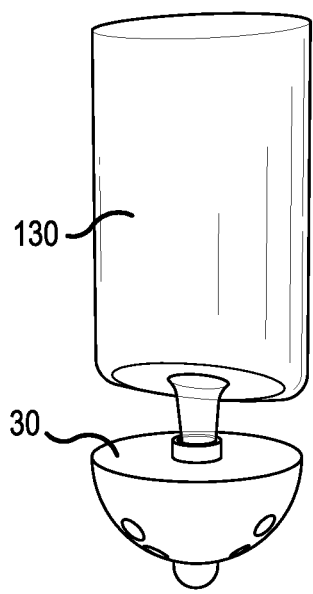
FIG. 2C shows a perspective view of the bottle solution dispenser attached to a dome of the assembly.
Figure 2D:
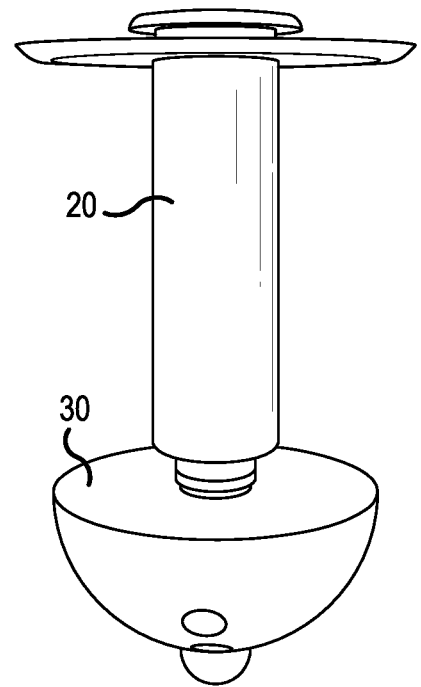
FIG. 2D shows a perspective view of the syringe solution dispenser attached to the dome of the assembly.

Referring now to FIGS. 2C and 2D, there are shown a perspective view of the bottle solution dispenser 130 attached to a dome 30 of the assembly (FIG. 2C) and a perspective view of the syringe solution dispenser 20 attached to the dome 30 of the assembly (FIG. 2D). As an exemplary first step of preparing the assembly for use, the bottle 130 or syringe 20 may be connected to the inlet port of the hollow dome 30, as shown.

Referring now to FIGS. 2E and 2F, there are shown a perspective view of the assembly in an upside-down orientation with an absorbent disc 40 attached to the dome of the assembly with the bottle solution dispenser 130 thereon (FIG. 2E) and a perspective view of the assembly in an upside-down orientation with the absorbent disc 40 attached to the dome of the assembly with the syringe solution dispenser 20 thereon (FIG. 2F). As an exemplary second step of preparing the assembly for use, the absorbent disc 40 may be applied to the hollow dome, as shown.

Figure 2G:
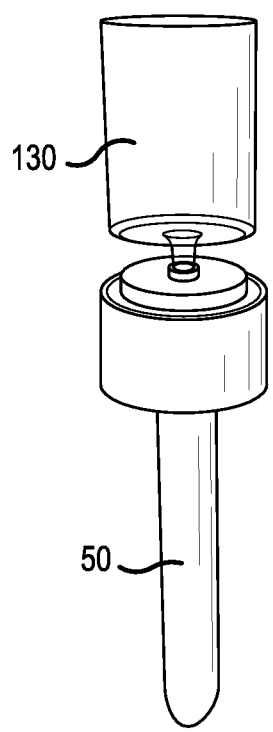
FIG. 2G shows a perspective view of the assembly secured to a proximal trocar port with the bottle solution dispenser thereon.
Figure 2H:
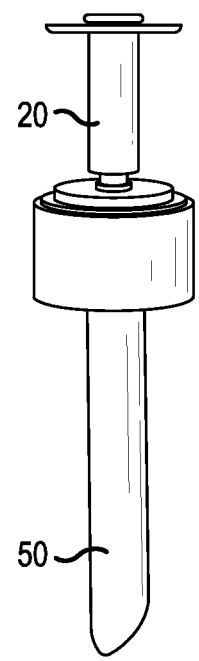
FIG. 2H shows a perspective view of the assembly secured to the proximal trocar port with the syringe solution dispenser thereon.

Referring now to FIGS. 2G and 2H, there are shown a perspective view of the assembly secured to a proximal trocar port with the bottle solution dispenser 130 thereon (FIG. 2G) and a perspective view of the assembly secured to the proximal trocar port with the syringe solution dispenser 20 thereon (FIG. 2H). As an exemplary third step of preparing the assembly for use, the absorbent disc may be applied to the proximal port of the trocar 50, and the solution delivered from the bottle 130 or syringe 20 through the inlet port of the hollow dome, through the interior of the hollow dome, and out of the outlet ports of the hollow dome to contact and wet the absorbent disc, as shown.

Figure 2I:
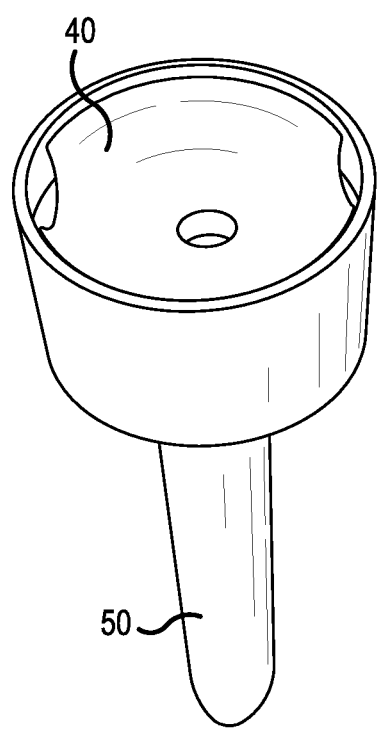
FIG. 2I shows an upper perspective view of a wetted disc secured to the proximal trocar port, ready for use by insertion of a telescope through the central aperture of the wetted disc.
Figure 2J:
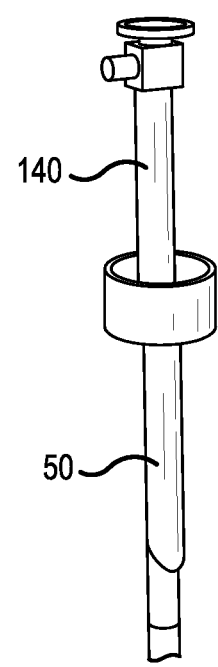
FIG. 2J shows a perspective view of the telescope inserted through the central aperture of the wetted disc as it is seated in the proximal trocar port.

Referring now to FIGS. 2I and 2J, there are shown an upper perspective view of a wetted disc secured to the proximal trocar port, ready for use by insertion of a telescope through the central aperture of the wetted disc 40 (FIG. 2I) and a perspective view of the telescope inserted through the central aperture of the wetted disc 40 as it is seated in the proximal trocar port (FIG. 2J). After the disc 40 is wetted and secured at the proximal port of the trocar 50, a telescope 140 may be inserted through the central aperture of the wetted disc 40 and into and through the trocar 50 for imaging within the body of the patient, as shown at FIG. 2J. In this configuration the telescope 140 may be used for the MIS technique, and may be slidingly removed from a portion of the trocar 50 to slidingly wipe away fog, condensation, and debris from the telescope 140 and/or an optical element of the telescope 140, such as a lens or optically transparent component, to restore light capture by the telescope 140 and vision by the surgeon or operator.

Figure 3C:
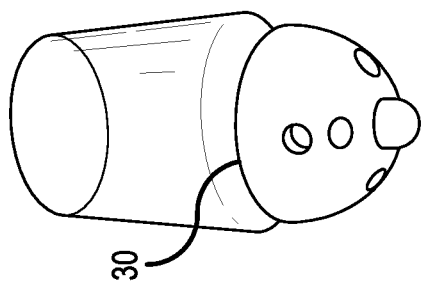
FIG. 3C shows a lower perspective view of a third hollow dome of an assembly of the present disclosure.
Figure 3B:
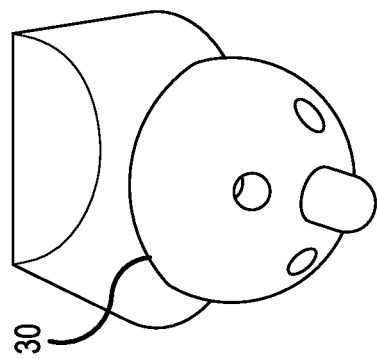
FIG. 3B shows a lower perspective view of a second hollow dome of an assembly of the present disclosure.
Figure 3A:
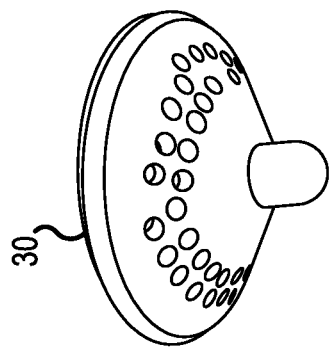
FIG. 3A shows a lower perspective view of a first hollow dome of an assembly of the present disclosure.
Figure 3F:
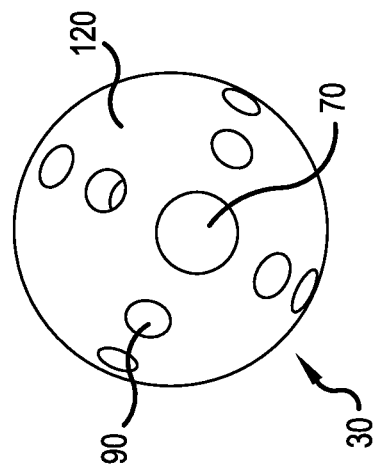
FIG. 3F shows a bottom view of the third hollow dome of an assembly of the present disclosure.
Figure 3E:
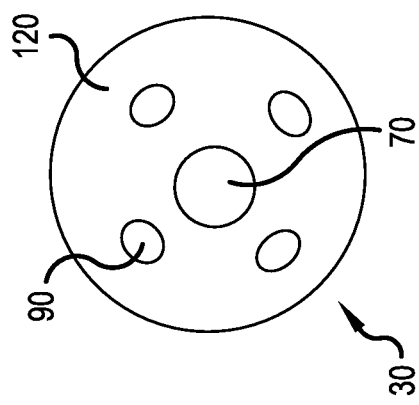
FIG. 3E shows a bottom view of the second hollow dome of an assembly of the present disclosure.
Figure 3D:
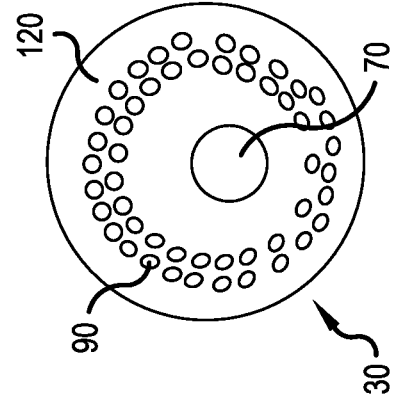
FIG. 3D shows a bottom view of the first hollow dome of an assembly of the present disclosure.
Figure 3I:
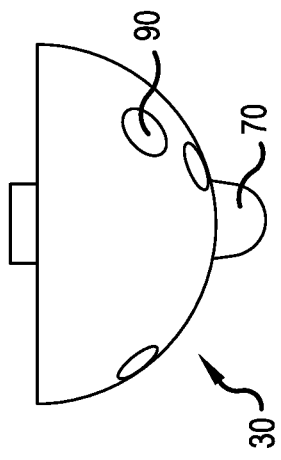
FIG. 3I shows a side cutaway view of the third hollow dome of an assembly of the present disclosure.
Figure 3H:
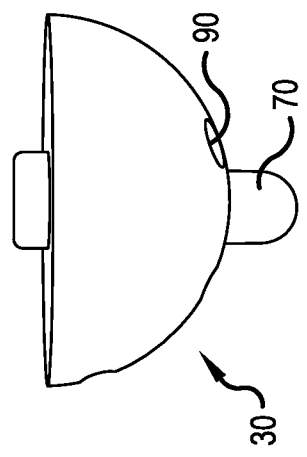
FIG. 3H shows a side cutaway view of the second hollow dome of an assembly of the present disclosure.
Figure 3G:
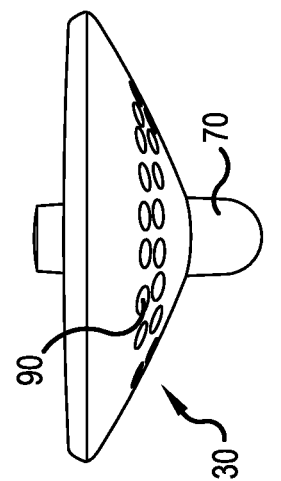
FIG. 3G shows a side cutaway view of the first hollow dome of an assembly of the present disclosure.
Figure 3L:
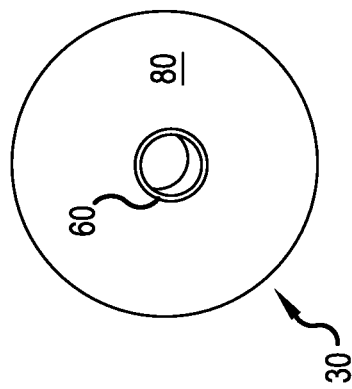
FIG. 3L shows a bottom view of the third hollow dome of an assembly of the present disclosure.
Figure 3K:
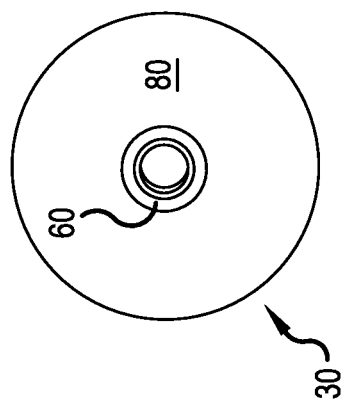
FIG. 3K shows a bottom view of the second hollow dome of an assembly of the present disclosure.
Figure 3J:
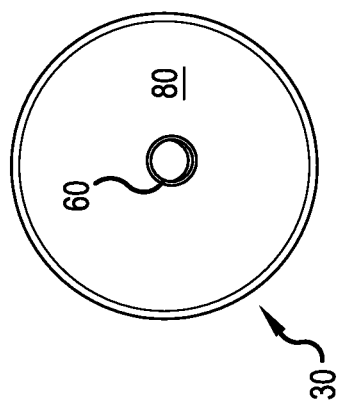
FIG. 3J shows a bottom view of the first hollow dome of an assembly of the present disclosure.

Referring now to FIGS. 3A, 3D, 3G, and 3J, there are shown a lower perspective view of a first hollow dome of an assembly of the present disclosure (FIG. 3A), a bottom view of the first hollow dome (FIG. 3D), a side cutaway view of the first hollow dome (FIG. 3G), and a bottom view of the first hollow dome (FIG. 3J). A first embodiment of a hollow dome 40 includes a plurality of outlet ports 90 regularly spaced along the slant (i.e., lower portion 120) of the hollow dome 40, arranged into an inner ring and an outer ring, as shown. The angle of the slant 120 relative to a vertical axis of the hollow dome 40, and/or the shape of the slant 120, may be varied as needed to configure the hollow dome 40 for use with a particular set of trocars or for use with any trocar from any designer (i.e., a universal fit). The plurality of smaller outlet ports 90 may be suitable for broad surface wetting of an absorbent disc.

Referring now to FIGS. 3B, 3E, 3H, and 3K, there are shown a lower perspective view of a second hollow dome of an assembly of the present disclosure (FIG. 3B), a bottom view of the second hollow dome (FIG. 3E), a side cutaway view of the second hollow dome (FIG. 3H), and a bottom view of the second hollow dome (FIG. 3K). A second embodiment of a hollow dome 40 includes a plurality of outlet ports 90 regularly spaced along a curved slant (i.e., lower portion 120) of the hollow dome 40, arranged into a ring, as shown. The second embodiment includes four larger outlet ports 90 which may be suitable for deep wetting of an absorbent disc.

Referring now to FIGS. 3C, 3F, 3I, and 3L, there are shown a lower perspective view of a third hollow dome of an assembly of the present disclosure (FIG. 3C), a bottom view of the third hollow dome (FIG. 3F), a side cutaway view of the third hollow dome (FIG. 3I), and a bottom view of the third hollow dome (FIG. 3L). A third embodiment of a hollow dome 40 includes a plurality of outlet ports 90 regularly spaced along the curved slant (i.e., lower portion 120) and arranged into an inner ring and an outer ring, as shown. The third embodiment includes two pairs of four larger outlet ports 90 which may be suitable for a balance of broad surface wetting and deep wetting of an absorbent disc.

In various embodiments, the hollow dome may be mostly or fully hollow, as shown, however, in alternate embodiments, may be substantially solid with channels therein for channeling the solution from the inlet port to the outlet ports. The selection of a mostly or fully hollow design may provide improved cost savings for manufacturing the hollow dome, however, the selection of a hollow dome that is mostly solid with channels therein may provide improved structural resilience to the dome such that it may not become deformed when a force is applied thereto, as may occur when the absorbent disc is secured to the proximal port of the trocar. In this manner, the term "hollow" herein, as it relates to the dome, generally may refer to a mostly or completely hollow dome or, in other instances, a mostly solid dome with channels therethrough for fluidly connecting the outlet ports to the inlet port.

Telescope Maintenance Methods

Figure 4:
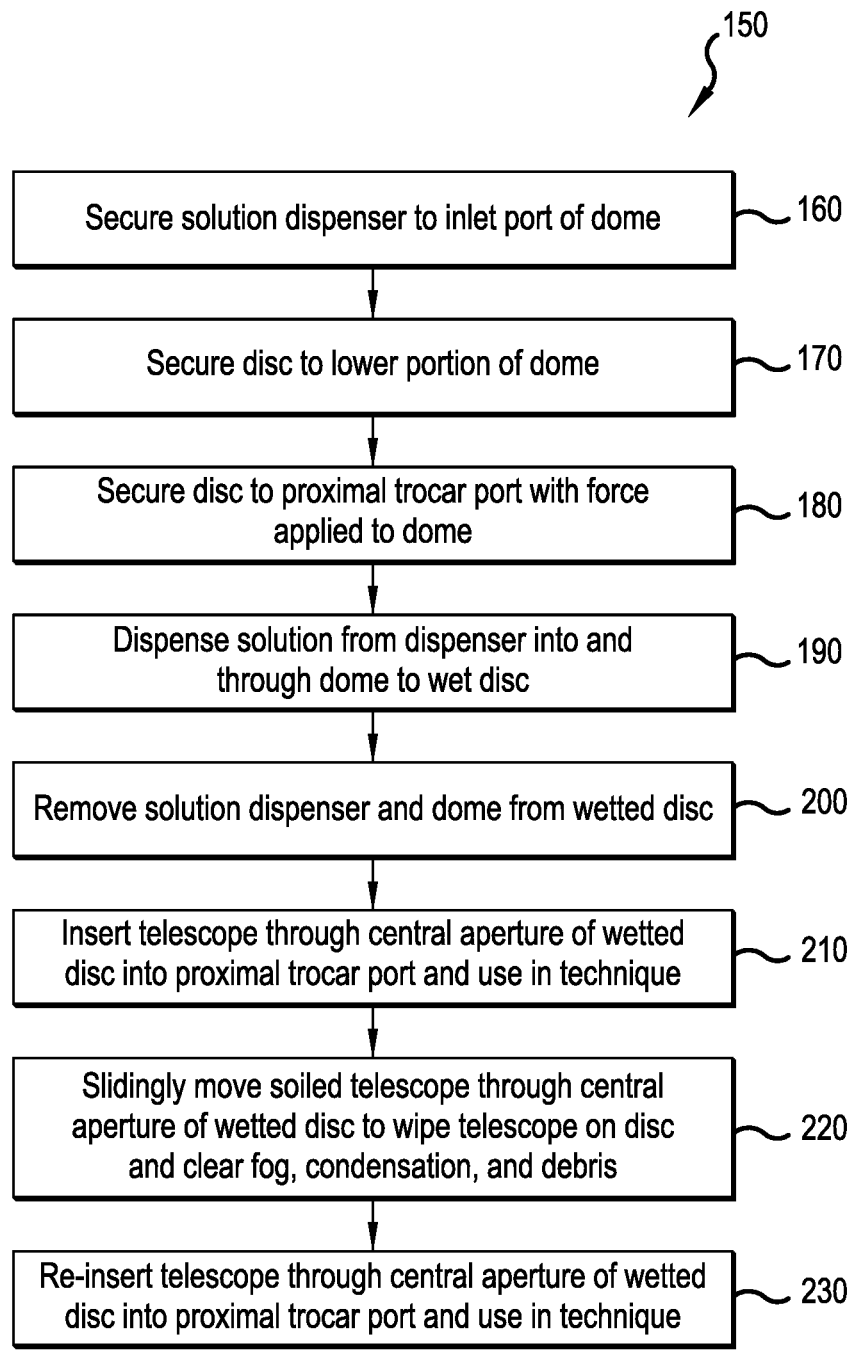
FIG. 4 shows a flow chart of an exemplary method for maintaining a telescope for a MIS technique, according to the present disclosure.

Referring now to FIG. 4, there is shown a flow chart of an exemplary method 150 for maintaining a telescope for a MIS technique, according to the present disclosure. A method 150 for maintaining a telescope for a minimally invasive surgery (MIS) technique generally may comprise securing 180 an absorbent disc about a proximal port of a trocar, wetting 190 the absorbent disc with a solution, and contacting 220 the telescope to the absorbent disc to remove fog, condensation, or debris from the telescope for continued use of the telescope in the MIS technique. The absorbent disc may generally include a central aperture configured to receive the telescope therethrough. In embodiments, the contacting 220 the telescope to the absorbent disc comprises slidingly moving the telescope through the central aperture to contact the absorbent disc against the telescope. In this manner, the telescope—and optical elements thereof such as lenses and other optically transparent parts—are easily cleaned for continued use.

In embodiments, the securing 180 the absorbent disc about the proximal port of the trocar comprises inserting a lower protrusion of a hollow dome into the central aperture and applying an attachment force to the hollow dome to seat the absorbent disc with the proximal port of the trocar. The hollow dome may be removed from the absorbent disc to leave the absorbent disc alone attached to the proximal port of the trocar by applying a removal force to lift and remove the hollow dome. In this manner, the dome (and, optionally, the dome with the syringe or bottle connected thereto) may be used to easily apply the disc to the trocar without necessarily snugly adhering the dome to the disc, and the dome can be removed after wetting the disc for use of the disc in the MIS procedure.

In embodiments, the wetting 190 the absorbent disc with the solution comprises fitting a slip tip connector of a syringe or a bottle to an inlet port of a hollow dome and delivering the solution from the syringe or the bottle through the inlet port into an interior of the hollow dome and out of a plurality of outlet ports to contact the absorbent disc. While the absorbent disc may be wetted without use of the dome, the use of the dome provides a more reliable and even wetting of the disc that can be easily repeated by a variety of individual with little or no requirement for advanced expertise or experience.

In various embodiments, additional steps of the method may be carried out, such as securing 160 the solution dispenser to the inlet port of the dome, securing 170 the disc to the lower portion of the dome, and removing 200 the solution dispenser and dome from the wetted disc to leave the wetted disc alone against the proximal trocar port. After the disc is wetted and adhered to the proximal trocar port, the telescope may be inserted 210 and used in a MIS technique. Once the telescope becomes fogged or otherwise soiled, it may be slidingly moved 220 through the central aperture of the wetted disc to clear away the fog, condensation, or debris for re-insertion 230 and continued use in the MIS technique. These operations may be repeated, in whole or in part, in any suitable order as needed by medical personnel without departing from the scope of the disclosure. For example, if repeated cleaning of the telescope soils the wetted disc, the wetted disc may be removed from the trocar and replaced with a new absorbent disc to be wetted and used anew, as would be understood by the person having ordinary skill in the art.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way appreciably intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications can be referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present disclosure is not entitled to antedate such publication by virtue of prior present disclosure. Further, the dates of publication provided herein can be different from the actual publication dates, which can require independent confirmation.

The patentable scope of the present disclosure is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

Insofar as the description above and the accompanying drawing disclose any additional subject matter that is not within the scope of the claims below, the disclosures are not dedicated to the public and the right to file one or more applications to claims such additional disclosures is reserved.

The foregoing descriptions of specific embodiments of the present invention have been presented for purposes of illustration and description. They are not intended to be exhaustive or to limit the present invention to the precise forms disclosed, and modifications and variations are possible in view of the above teaching. The exemplary embodiment was chosen and described to best explain the principles of the present invention and its practical application, to thereby enable others skilled in the art to best utilize the present invention and its embodiments with modifications as suited to the use contemplated.

It is therefore submitted that the present invention has been shown and described in the most practical and exemplary embodiments. It should be recognized that departures may be made which fall within the scope of the invention.

With respect to the description provided herein, it is submitted that the optimal features of the invention include variations in size, materials, shape, form, function and manner of operation, assembly, and use. All structures, functions, and relationships equivalent or essentially equivalent to those disclosed are intended to be encompassed by the present invention.

The following is claimed:

1. An assembly for maintaining a telescope for a minimally invasive surgery (MIS) technique, the assembly comprising:
   a hollow dome, wherein the hollow dome has:
   an upper portion,
   an inlet port in the upper portion,
   wherein the inlet port is configured to connect with a slip tip connector of a syringe or a bottle for delivery of a solution through the inlet port,
   a lower protrusion,
   a slanted portion between the upper portion and the lower protrusion,
   an interior formed by the upper portion, the slanted portion and the lower protrusion, and
   a plurality of outlet ports on the slanted portion that extend away from a surface of the upper portion and the interior; and
   an absorbent disc,
   wherein the absorbent disc has a central aperture and is configured to be wetted by delivery of a solution through the inlet port to the interior of the hollow dome and out of the plurality of outlet ports to contact and wet the absorbent disc, the absorbent disc is configured to use the solution when the absorbent disc is in contact with the telescope to clean the telescope and to circumscribe the telescope such that the telescope may be partially slidably removed without completely removing the telescope from a trocar.

2. The assembly of claim 1, wherein the hollow dome is at least approximately cone-shaped, the inlet port is positioned centrally at the upper portion thereof, and the lower protrusion is positioned centrally at a lower portion thereof.

3. The assembly of claim 1, wherein the hollow dome fits snugly with the absorbent disc such that the plurality of outlet ports directly contacts portions of the absorbent disc when applied thereto.

4. The assembly of claim 1, wherein the plurality of outlet ports are regularly spaced along a circumference of the slanted portion of the hollow dome.

5. The assembly of claim 1, wherein the plurality of outlet ports includes an inner ring of outlet ports and an outer ring of outlet ports, wherein a distance from the inner ring of outlet ports to the lower protrusion is less than a distance from the outer ring of outlet ports to the lower protrusion.

6. The assembly of claim 1, wherein the central aperture is configured to slidingly accept the telescope therethrough.

7. The assembly of claim 6, wherein a sliding movement of the telescope through the central aperture contacts the absorbent disc against the telescope and clears fog or debris from the telescope for continued use of the telescope in the MIS technique.

* * * * *